United States Patent [19]

Schawartz et al.

[11] 4,049,639

[45] Sept. 20, 1977

[54] 5-AMIDO IMIDO TRIAZENE TRIAZOLES AND PYRAZOLES WITH PHOTOGRAPHIC AND ANTIMYCOTIC UTILITY

[75] Inventors: József Schawartz; Maria Hornyák; Éva Majorszki; Erzsebet Kovacsovics; Ágoston Dávid; Gábor Horváth, all of Budapest, Hungary

[73] Assignee: Chinoin Gyogyszer es Vegyeszeti Termekek Gyara Rt, Budapest, Hungary

[21] Appl. No.: 549,761

[22] Filed: Feb. 13, 1975

Related U.S. Application Data

[63] Continuation-in-part of Ser. No. 302,724, Nov. 1, 1972, abandoned.

[30] Foreign Application Priority Data

Nov. 19, 1971 Hungary .................. CI 1190

[51] Int. Cl.² .............. C07C 107/00; C07C 107/04; G03C 5/30
[52] U.S. Cl. .................... 260/140; 96/66 R; 96/66 HD; 260/308 A; 260/309; 260/310 B; 424/226; 548/335
[58] Field of Search ......................... 260/140

[56] References Cited

U.S. PATENT DOCUMENTS

| 2,120,808 | 6/1939 | Lecher ................. 260/140 X |
| 2,154,405 | 4/1939 | Lecher et al. .......... 260/140 X |
| 2,199,003 | 4/1940 | Lecher et al. .......... 260/140 |
| 2,299,244 | 10/1942 | McClellan et al. ...... 260/140 |
| 2,339,934 | 1/1944 | McClellan et al. ...... 260/140 |
| 2,923,694 | 2/1960 | Schmidt ............... 260/140 X |
| 3,313,690 | 4/1967 | Vogel et al. .......... 260/140 X |

OTHER PUBLICATIONS

Shealy et al., J. Org. Chem., vol. 27, pp. 2150 to 2154 (1962).
Shealy et al., J. Med. Chem., vol. 9, pp. 34 to 38 (1966).

*Primary Examiner*—Floyd D. Higel
*Attorney, Agent, or Firm*—Karl F. Ross

[57] ABSTRACT

Triazene derivatives of the formula

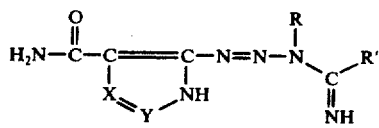

wherein
X is = CH— or nitrogen,
Y is —CH = or nitrogen,
R and R' are substituted or unsubstituted alkyl, aryl, arakyl or cycloarkyl. The compounds are effective as photographic toners and additives to photographic developers and as antimycotic agents in animal therapy.

19 Claims, No Drawings

5-AMIDO IMIDO TRIAZENE TRIAZOLES AND PYRAZOLES WITH PHOTOGRAPHIC AND ANTIMYCOTIC UTILITY

CROSS-REFERENCE TO RELATED APPLICATION

This application is a continuation-in-part of application Ser. No. 302,724 filed Nov. 1, 1972, now abandoned.

FIELD OF THE INVENTION

This invention is directed to new triazene derivatives.

BACKGROUND OF THE INVENTION

It is known from the literature, that 5-diazo-imidazole-4-carboxamide (J. Org. Chem. 26 1961), 5-diazo-1H-1, 2, 3-triazolyl-4-carboxamide (J. Med. Chem. 9, 733; 1966) and 3-diazo-pyrazol-4-carboxamide and its tautomeric forms react with dialkylamines to form 1,3-disubstituted triazenes.

DESCRIPTION OF THE INVENTION

The present invention provides a new compound of the Formula I

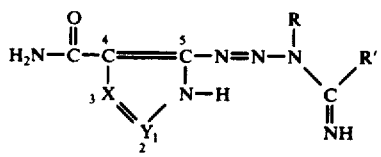

wherein
X is a =CH-group or nitrogen;
Y is a -CH= group or nitrogen;
R is a substituted or unsubstituted alkyl, aralkyl, cycloalkyl or aryl group; and
R' is a substituted or unsubstituted alkyl, aralkyl, cycloalkyl or aryl group.

According to the invention
X is = CH— or nitrogen;
Y is —CH= or nitrogen;
R is $C_1$ to $C_6$ alkyl, a $C_3$ to $C_6$ cycloalkyl or unsubstituted or halosubstituted phenyl, and
R' is $C_1$ to $C_6$ alkyl or unsubstituted phenyl or phenyl substituted with $C_1$ to $C_6$ alkoxy or $C_1$ to $C_6$ alkyl.

According to a further aspect of the present invention there is provided a process for the preparation of a new compound of the Formula I, wherein
X is =CH— or nitrogen;
Y is an =CH—group or nitrogen;
R is a substituted or unsubstituted alkyl, aralkyl, cycloalkyl or aryl group; and
R' is an unsubstituted or substituted alkyl, aralkyl, cycloalkyl or aryl group,
which comprises reacting a diazoheterocyclic compound of the formula II

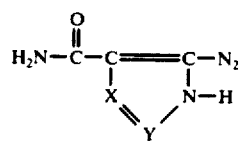

wherein

X and Y have the meanings stated above, with an amidine of the formula III

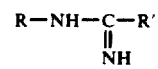

wherein
R and R' have the meanings stated above.

R and R' are preferably straight chain or branched chain alkyl group with 1-6 carbon atoms or cycloalkyl with 3-6 carbon atoms, aralkyl containing an alkyl chain with 1-3 carbon atoms or an aryl group with 6-10 atoms.

The groups R and R' preferably represent methyl, ethyl, propyl, n-butyl, isobutyl cyclopentyl, cyclohexyl, phenyl or naphthyl groups. These groups may be unsubstituted or substituted with one or more substituents.

The alkyl group may be substituted with hydroxy, amino or nitro or a halogen (F, Cl, Br, I). The substituents of the aryl and the aryl ring of the aralkyl group may be selected from the group consisting of alkyl ($C_1$–$C_6$), alkoxy ($C_1$–$C_6$), nitro, amino, hydroxy or halogen (F, Cl, Br, I).

R is preferably alkyl with 1-6 carbon atoms, (e.g., n-butyl), cycloalkyl with 3-6 carbon atoms (e.g., cyclohexyl group or phenyl). In the compounds R' is preferably an alkyl with 1-4 carbon atoms (e.g., methyl) or phenyl, which is unsubstituted or may be substituted with one or more alkyl ($C_1$–$C_6$) groups.

Particularly advantageous representatives of the compounds of the formula I are mentioned in the Examples.

Preferably the reaction is carried out in an organic solvent. Preferred solvents are the alkanols, particularly methanol or ethanol. The reaction may be carried out at 0°-50° C, preferably at 20°-30° C.

Most advantageously a diazo compound of the formula II is added to an alcoholic solution of an amidine of the formula III whereby, after a quick dissolution, the reaction takes place within several hours.

According to another embodiment of the present invention, the amidine of the general formula III is set free from its salt, preferably from its hydrochloride — with a base — preferably with an alkali-metal base— and the amidine is reacted in situ with the diazo compound.

The working up of the reaction mixture may be carried out by usual known methods. The triazenes of the formula I are generally obtained after evaporating the solution in vacuo to a thick resin, which may be converted into an easily filterable crystalline product with acetone or ethylacetate.

According to another embodiment the residue obtained after evaporation of diluent may be crystallized from a solvent or a solvent mixture. Preferred solvents are the alcohols (methyl, ethyl, propyl, butyl,) acetone, ethyl acetate, ethers (methyl, ethyl, propyl butyl) or mixtures thereof.

The compounds of the formula I are, in pure form, colorless crystalline materials, which melt under decomposition.

The compounds of the general formula I may be used in compositions comprising the active ingredient and inert, solid or liquid diluents or carriers. As a carrier one may use water, gelatin, talc, magnesium stearate, calcium carbonate, etc. The compositions may be prepared according to any method known in the art for the manufacture of pharmaceutical compositions, such as tablets, capsules, dragees, solutions, emulsions, suspensions, and suppositories. The compositions may be suitable for enteral, parenteral or rectal administration.

The compounds of the formula I may be used in photography for development of color films and as additives to modify shades of colors. The present invention is directed furthermore to developers of color films, which comprise in addition to the usual components also a compound of the formula I. The present invention is directed furthermore to additives to develop color films, which comprise a compound of the formula I.

The photographic utility is effectively demonstrated by introducing any of the compounds defined by the formula I into a developer solution for color development as a toner. For example, when the compound of Example 3 is added to a KINOCOLOR developer solution for ORWO color film a grayish violet cast is produced when it is added to an AGFA GAVAERT color film developing solution gives a greenish shade of violet. The compound of Example 5 (below) likewise imparts a grayish cast to ORWO color film and a grayish-green cast to an AGFA GAVAERT color film using the KINOCOLOR developer solution.

The antimycotic qualities of the compounds of the formula I have been demonstrated for a wide variety of fungi. The products may be used internally in daily dosages of 0.1 microgram per kilogram of body weight in animal therapy for treatment of fungus conditions or may be externally applied in conventional pharmaceutical excipients such as lotions and the like for the treatment of fungi.

EXAMPLES

Further details of our process are to be found in the Examples:

EXAMPLE 1

1.2 g. of N-butyl-acetamidine (Bp.: 76°–78° C/0.4 torr) are dissolved in 50 ml of anhydrous ethanol, whereafter 1.4 g. of 5-diazo-imidazole-4-carboxamide are added at 25° C under stirring within 10 minutes. After 2.5 hours the orange-colored solution is clarified with activated charcoal and evaporated in vacuo. 2.6 g. of a slowly crystallizing resin are obtained, which is twice crystallized from an ethanol-acetone mixture. Thus, a colorless, crystalline product, the 5-[3-n-butyl-3-(alpha-iminoethyl)-1-triazeno]-imidazole-4-carboxamide, melting at 191° C, is obtained (decomposition)

EXAMPLE 2

2.84 g. of finely powdered N-butyl-4-n-butoxy-benzamidine-chlorhydrate are admixed with 3.15 ml of a mixture of methanol and sodium methylate (0.23 g. Na) at room temperature within 15 minutes, whereupon the reaction mixture is diluted with 50 ml of anhydrous ethanol and kept at 0° C half an hour. The sodium chloride is filtered off and 1.4 g. of 5-diazo-imidazole-carboxamide are added to the alcoholic solution obtained. After 2 hours the solution is clarified with activated charcoal, whereupon the solution obtained is evaporated in vacuo and the mass obtained is admixed with a mixture of 20 ml of acetone and 10 ml of ether. The colorless product obtained [3.4 g.; m.p. 140° C, decomp.] is recrystallized from a mixture of acetone and ethanol. Thus 5-[3-n-butyl-3-(4'-n-butoxy-benzimido)-1-triazeno]-imidazole-4-carboxamide is obtained. M.p.: 142° C (decomposition).

EXAMPLE 3

3.10 g. of N-cyclohexyl-4-n-butoxy-benzamidine-chlorhydrate are worked up as described in Example 2. The alcoholic solution obtained is evaporated in vacuo and the mass obtained is admixed with a mixture of 20 ml of acetone and 10 ml of ether. The crude product (3.9 g., melting at 130° C, decomposition) is recrystallized from a mixture of 67 ml of acetone and 7 ml of anhydrous ethanol. Thus 2.7 g. of 5-[3-cyclohexyl-3-(4'-n-butoxy-benximido)-1-triazeno-] imidazole-4-carboxamide melting at 132° C (decomposition) are obtained.

The compound of Example 3 was added in an amount of 10 to 100 milligrams to 100 milliliters of a KINOCOLOR developer solution (registered trademark, commerically available from REANAL FINOM, Budapest, HUNGARY) for the development of conventionally exposed ORWO color film and AGFA GAVAERT color film. The product imparted a grayish violet color to the ORWO film with a violet intensity increasing with the concentration of the compound of Example III. The AGFA GAVAERT color film received a greenish shade of color with the green intensity increasing with the concentration of the additive.

EXAMPLE 4

5.7 g. of N-butyl-acetamidine are dissolved in 300 ml of anhydrous ethanol, whereupon 7 g. of 5-diazo-1,2,3-triazole-4-carboxamide are added at 25° C within half an hour. After 3 hours the solution is clarified with activated charcoal and evaporated in vacuo. The residual thick oil is admixed with 40 ml of anhydrous ethylacetate and the crude product (9.7 g. melting at 150° C decomposition) is recrystallized from a mixture of 110 ml of acetone and 40 ml of anhydrous ethanol. Thus 6.1 g. of 5-[3-n-butyl-3-(alpha-iminoethyl)-1-triazeno]-1,2,3-triazole-4-carboxamide melting at 159°–160° C (decomposition) are obtained.

EXAMPLE 5

8.5 g. of N-butyl-4-n-butoxy-benzamidine-chlorohydrate are dissolved in 10 ml of 3.06 N sodium methylate in methanol as described in Exampe 2. The alcoholic amidine solution obtained is reacted with 4.2 g. of 5-diazo-1,2,3-triazole-4-carboxamide. The alcoholic solution is evaporated in vacuo and the residue is admixed with 30 ml of anhydrous ethyl acetate. 10.35 g. of the crude triazene (melting at 158°–160° C, decomposition) obtained are recrystallized from a mixture of ethyl acetate and anhydrous ethanol. Thus 8.45 g. of 5-[3-n-butyl-3-(4'-n-butoxy-benzimido)-1-triazeno]-1,2,3-triazole-4-carboxamide melting at 160° C (decomposition) are obtained.

The compound of Example 5 was tested with KINOCOLOR developer for ORWO and AGFA GAVAERT color film. As described in Example 3. The ORWO color film received a grayish cast and the Agfa Gavaert color film a grayish-green shade of color.

EXAMPLE 6

3.10 g. of N-cyclohexyl-4-n-butoxy-benzamidine-chlorohydrate are worked up as described in Example 2. The alcoholic amidine solution obtained is reacted with 1.4 g. of 5-diazo-1,2,3-triazole-4-carboxamide, whereupon the crude triazene obtained (4 g.) are recrystallized from 23 ml of acetone. Thus 3.0 g. of 5-[3- cyclohexyl-3-(4'-butoxy-benzimido)-1-triazeno]-1,2,3-triazole-4-carboxamide melting at 159° C (decomposition) are obtained.

EXAMPLE 7

3.05 g. of N-phenyl-4-n-butoxy-benzamidine-chlorohydrate and 1.4 g. of 5-diazo-1,2,3-triazole-4-carboxamide are reacted as described in Example 2. The product is recrystallized from ethyl acetate. Thus 3.10 g. of 5-[3-phenyl-3-(4'-n-butoxy-benzimido)-1-triazeno]-1,2,3-triazole-4-carboxamide melting at 150° C (decomposition) are obtained.

EXAMPLE 8

2.86 g. of N-butyl-3-ethyl-4-methoxy-benzamidine-chlorohydrate and 1.4 g. of 5-diazo-1,2,3-triazole-4-carboxamide are reacted as described in Example 2. The crude product (3.5 g.), melting at 112° C decomposition obtained are recrystallized twice from acetone. Thus 1.5 g. of 5-[3-butyl-3-(3'-ethyl-4'-methoxy-benzimido)-1-triazeno]-1,2,3-triazole-4-carboxamide melting at 115° C (decomposition) are obtained.

EXAMPLE 9

1.2 g. of N-butyl-acetamidine are dissolved in 50 ml of ethanol, whereupon 1.4 g. of 3-(5)-diazo-pyrazole-4-carboxamide are added and after 3 hours the mixtures is clarified with activated characoal. The solution obtained is evaporated in vacuo and the residual oil (2.5 g.) is recrystallized from a mixture of 10 ml of anhydrous ethanol, 10 ml of acetone and 20 ml of ether. Thus 2.0 g. of 3-(5)-[3-n-butyl-3-(alpha-ininoethyl)-1-triazeno]-pyrazole-4-carboxamide, melting at 182° C (decomposition) are obtained.

EXAMPLE 10

2.84 g. of N-butyl-4-n-butyloxy-benzamidine-chlorohydrate are worked up as described in Example 2. The alcoholic amidine solution obtained is reacted with 1.4 g. of 3-(5)-diazo-pyrazole-4-carboxamide, whereupon the reaction mixture is evaporated in vacuo and the residual oil is admixed with 10 ml of acetone. The crude triazene (3.5 g.) melting at 118°-120° C (decomposition) is recrystallized from acetone. Thus 2.5 g. of 3-(5)-[3-n-butyl-3-(4'-n-butoxy-benzimido)-1-triazeno]-pyrazole-4-carboxamide, melting at 119° C (decomposition), are obtained.

EXAMPLE 11

3.10 g. of N-cyclohexyl-4-butoxy-benzamidine-chlorohydrate are worked up as described in Example 2. The alcoholic amidine solution obtained is reacted with 1.4 g. of 3-(5)-diazo-pyrazole-4-carboxamide at 25° C for 3 hours, whereupon the reaction mixture is clarified with charcoal and the solution is evaporated in vacuo. The resin obtained is recrystallized twice from acetone. Thus 3.5 g. of 3-(5)-[3-cyclohexyl-3-(4'-n-butoxy-benzimido)-1-triazeno]-pyrazole-4-carboxamide, melting at 116°-117° C (decomposition) are obtained.

EXAMPLE 12

From 1.7 g. of N-p-chlorophenyl-4-n-butoxy-benzamidinehydrochloride (mp.: 217° C) and 0.7 g. of 5-diazo-1,2,3-triazolo-4-carboxamide, 1.75 g. of 3-(5-[3-p-chlorophenyl-3-p-chlorophenyl-3-(4-n-butoxabenzimido)-1-triazeno])-1,2,3-triazole-4-carboxamide are obtained. Mp.: 173° C (decomposition). The process is carried out in an analogous manner to the preceding examples. On recrystallization from a mixture of ethyl acetate and anhydrous ethanol colorless crystals are obtained.

This compound is effective against filamental fungi in a concentration of 100 μg/ml. It inhibits the growth of yeast fungi in a concentration of 1000 μg/ml.

EXAMPLE 13

1.86 of N-[3', 4'-dichloro-phenyl]-4-n-butoxy-benzamidine-hydrochloride [mp.: 218° C] and 0.7 g. of 5-diazo-1,2,3-triazole-4-carboxamide are reacted in an analogous manner to the preceding examples. The resinous product obtained [2.4 g] is treated with 15 ml of acetone to yield 1.87 g. of a colorless crystalline substance, which is crystallized from a mixture of 35 ml of ethyl acetate and 18 ml of anhydrous ethanol. Thus 1.30 of 3-{5-[3', 4'-dichlorophenyl-3-(4-n-butoxy-benzimido)-1-triazeno]}-1,2,3-triazole-4-carboxamide are obtained.

This compound inhibits the growth of filamental fungi in a concentration of 10 μg/ml, and that of yeast fungi in a concentration of 100 μg/ml.

The inhibition of the growth of fungi was tested on a nutrient medium containing yeast, the nutrient medium contains 0.5% of yeast, 0.5% of glucose and 2% of agar, pH =7.

The 3-[5-(3,4-dichloro-phenyl)-3-(n-butoxy-benzimido)-1-triazeno]-1,2,3-triazole-4-carboxamide shows the following minimal inhibition concentration against various filamental fungi:

|  | μg/ml |
| --- | --- |
| Sacharomyces cerevisiae | 50–100 |
| Candida albicans | 50–100 |
| Candida utilis | 50–100 |
| Geotrichum candidum | 50–100 |
| Trichophyton mentagrophytes | 12.5 |
| Trichophyton rumbrum | 12.5 |
| Epidermophyton floccosum | 25 |
| Actinomucor repens | 50–100 |
| Aspergillus niger | 50–100 |
| Alternaria tenuis | 50–100 |
| Asochyta pisi | 25 |
| Cercospora beticola | 25 |
| Colletotrichon lini | 25 |
| Fusarium moniliformiae | 50–100 |
| Stemphylium radicinum | 25 |

We claim:

1. A compound of the formula:

$$H_2N-\underset{\|}{C}-\underset{\underset{Y}{\overset{X}{\|}}}{C}\underset{NH}{=}C-N=N-\underset{\underset{NH}{\overset{R}{\|}}}{N}\underset{C}{\overset{R}{\diagdown}}R'$$

wherein:

X is —CH= or nitrogen;

Y is =CH— or nitrogen;

R is $C_1$ to $C_6$ alkyl, $C_3$ to $C_6$ cycloalkyl, phenyl or halophenyl; and

R' is phenyl or phenyl substituted by $C_1$ to $C_6$ alkoxy or $C_1$ to $C_6$ alkyl, or is $C_1$ to $C_6$ alkyl.

2. A compound as defined in claim 1 wherein: R and R' are each selected from the group which consists of: methyl, ethyl, propyl, n-butyl, isobutyl, cyclopentyl, cyclohexyl and phenyl.

3. A compound of the formula:

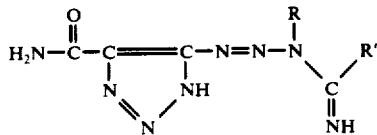

wherein:
R is $C_1$ to $C_6$ alkyl, $C_3$ to $C_6$ cycloalkyl, phenyl or halophenyl; and
R' is phenyl or phenyl substituted by $C_1$ to $C_6$ alkoxy or $C_1$ to $C_6$ alkyl, or is $C_1$ to $C_6$ alkyl.

4. A compound as defined in claim 3 wherein R and R' are each selected from the group which consists of: methyl, ethyl, propyl, n-butyl, isobutyl, cyclopentyl, cyclohexyl and phenyl.

5. A compound of the formula:

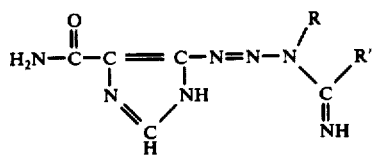

wherein:
R is $C_1$ to $C_6$ alkyl, $C_3$ to $C_6$ cycloalkyl, phenyl or halophenyl; and
R' is phenyl or phenyl substituted by $C_1$ to $C_6$ alkoxy, or $C_1$ to $C_6$ alkyl, or is $C_1$ to $C_6$ alkyl.

6. A compound as defined in claim 5 wherein R and R' are each selected from the group which consists of: methyl, ethyl, propyl, n-butyl, isobutyl, cyclopentyl, cyclohexyl and phenyl.

7. A compound of the formula:

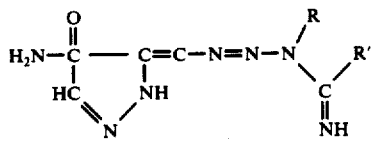

wherein:
R is $C_1$ to $C_6$ alkyl, $C_3$ to $C_6$ cycloalkyl, phenyl or halophenyl; and
R' is phenyl or phenyl substituted by $C_1$ to $C_6$ alkoxy, or $C_1$ to $C_6$ alkyl, or is $C_1$ to $C_6$ alkyl.

8. A compound as defined in claim 7 wherein R and R' are each selected from the group which consists of: methyl, ethyl, propyl, n-butyl, isobutyl, cyclopentyl, cyclohexyl and phenyl.

9. The compound defined in claim 1 which consists of: 5-[3-n-butyl-3-alpha-iminoethyl-1-triazeno]-imidazole-4-carboxamide.

10. The compound defined in claim 1 which consists of: 5-[3-n-butyl-3-(4'-butoxy-benzimido)-1-triazeno]-imidazole-4-carboxamide.

11. The compound defined in claim 1 which consists of: 5-[3-cyclohexyl-3-(4'-n-butoxy-benzimido)-1-triazeno]-imidazole-4-carboxamide.

12. The compound defined in claim 1 which consists of: 5-[3-n-butyl-3-(alpha-iminoethyl)-1-triazeno]-1,2,3-triazole-4-carboxamide.

13. The compound defined in claim 1 which consists of: 5-[3-n-butyl-3-(4'-n-butoxy-benzimido)-1-triazeno]-1,2,3-triazole-4-carboxamide.

14. The compound defined in claim 1 which consists of: 5-[3-cyclohexyl-3-(4'-butoxy-benzimido)-1-triazeno]-1,2,3-triazole-4-carboxamide.

15. The compound defined in claim 1 which consists of: 5-[3-phenyl-3-(4'-n-butoxy-benzimido)-triazeno]-1,2,3-triazole-4-carboxamide.

16. The compound defined in claim 1 which consists of: 5-[3-butyl-3-(3'-ethyl-4'-methoxy-benzimido)-1-triazeno]-1,2,3-triazole-4-carboxamide.

17. The compound defined in claim 1 which consists of: 3-(5)-[3-n-butyl-3(alpha-iminoethyl)-1-triazeno]-pyrazole-4-carboxamide.

18. The compound defined in claim 1 which consists of: 3-(5)-[3-n-butyl-3-(4'-n-butoxy-benzimido)-1-triazeno]-pyrazole-4-carboxamide.

19. The compound defined in claim 1 which consists of: 3-(5)-[3-cyclohexyl-3-(4'-n-butoxy-benzimido)-1-triazeno]-pyrazole-4-carboxamide.

* * * * *